United States Patent
Dahl et al.

(10) Patent No.: US 8,334,979 B2
(45) Date of Patent: Dec. 18, 2012

(54) METHOD FOR CONTROLLING THE REGISTER BETWEEN A PRINTED PATTERN AND A THREE-DIMENSIONAL PATTERN ON A PACKAGING MATERIAL

(75) Inventors: Magnus Dahl, Staffanstorp (SE); Lars Palm, Åkarp (SE); Gabor Benkö, Lund (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 373 days.

(21) Appl. No.: 12/808,329

(22) PCT Filed: Dec. 17, 2008

(86) PCT No.: PCT/SE2008/000710
§ 371 (c)(1), (2), (4) Date: Jun. 15, 2010

(87) PCT Pub. No.: WO2009/093936
PCT Pub. Date: Jul. 30, 2009

(65) Prior Publication Data
US 2010/0257987 A1    Oct. 14, 2010

(30) Foreign Application Priority Data
Jan. 23, 2008  (SE) .................................. 0800154

(51) Int. Cl.
*G01N 21/84* (2006.01)
(52) U.S. Cl. ...................................................... 356/429
(58) Field of Classification Search ............ 356/429
See application file for complete search history.

(56) References Cited

U.S. PATENT DOCUMENTS

| | | |
|---|---|---|
| 5,767,975 A | 6/1998 | Ahlen |
| 6,797,976 B2 * | 9/2004 | Pechan et al. ............ 250/559.45 |
| 2006/0032928 A1 | 2/2006 | Schaedel |

FOREIGN PATENT DOCUMENTS

WO    WO 01/51275 A1    7/2001

OTHER PUBLICATIONS

International Search Report issued by Swedish Patent Office on Apr. 23, 2009 as the International Searching Authority for International Application No. PCT/SE2008/000710.

* cited by examiner

*Primary Examiner* — Roy M Punnoose
(74) *Attorney, Agent, or Firm* — Buchanan Ingersoll & Rooney PC

(57) ABSTRACT

A method and/or an apparatus for controlling the register between print and three-dimensional structures, such as creases in the forming of a package, and a method and/or the apparatus for controlling a unit for repeated cutting-out or perforation of a material web from which the packages are formed. In the control, a focused, high intensive light beam, such as a laser line, is laid in a bisecting direction to relevant creases. The position of the crease or the creases is determined by sensing of a deflection of the projected laser line. Diffuse light from the laser line may be used in order to register the position of a register marking. If the difference between the register marking and crease differs more than a predetermined value, the creasing tool and/or printing press is automatically adjusted.

20 Claims, 2 Drawing Sheets

METHOD FOR CONTROLLING THE REGISTER BETWEEN A PRINTED PATTERN AND A THREE-DIMENSIONAL PATTERN ON A PACKAGING MATERIAL

TECHNICAL FIELD

The present invention relates to a method and an apparatus for controlling the register between a printed pattern and three-dimensional structures, for example creases and holes, in a package. The present invention also relates to a method where the control is employed in controlling repeated cuttings on a material web in motion.

BACKGROUND ART

When blanks are to be formed for different types of packaging containers, a material web will, at some point in the conversion process, be provided with fold indications, so-called creases, and possibly also with holes intended for opening devices. A blank which is cut out from the web will then be folded along the creases in order to form a finished packaging container. In particular, this relates to a material web consisting of, or including, a paper or paperboard layer for the manufacture of laminated packaging materials suitable for packing liquid foods. In addition to the creases, the material web is also provided with printed patterns, and so a number of creasing devices, often rollers, are coordinated with a printing press. In order for the finished packaging container to obtain the desired appearance and configuration, with the printed pattern correctly positioned, it is crucial that printed pattern, creases and possible holes are correctly positioned in relation to one another on the material web. In a subsequent forming of packages, it is crucial that printed pattern, creases and holes are in correct mutual relationships or register so as not to disrupt the function of a subsequent filling machine and in order for the printed pattern and the creases to arrive at their intended positions on the final package. Today, this fine adjustment of printed pattern and creases in relation to one another takes place substantially manually when the printing press is made ready for a run. During the run, no control is normally made of whether the printed pattern and creases lie in the correct relationship to one another, which may result in many of the packaging containers departing from the packing and filling machine with more or less incorrect conformity between the printed decorative pattern and the crease pattern, or the holes.

The crease lines extend transversely, or diagonally across, or alternatively longitudinally of the direction of movement of the material web, and the positions of the holes (if any) may be optionally sited between the crease lines.

Holes intended for opening devices may be made in the material web in different ways. Traditionally, the holes are punched mechanically in the same, or a similar operation, as the material web is provided with fold indications. According to more recent technology, holes are cut out in a subsequent operation downstream of the conversion of the material web, this conversion resulting in a laminated packaging material.

BRIEF SUMMARY OF THE INVENTION

One object of the present invention is to facilitate the monitoring and control of the register between a printed pattern, and three-dimensional structures such as creases and/or holes, and to carry out corrections where necessary. This is put into effect continuously during operation. Moreover, use is made of one and the same equipment for identifying the position of both the printed pattern and the creases/the holes. The holes may be mechanically punched or formed using other suitable hole-making equipment.

In order to identify the three-dimensional structures, in particular the creases but also the holes (if any), and register their positions, use is made of triangulation technology. According to the present invention, use is made of a high-intensity, focused light source, such as for example a laser light source or an LED (Light Emitting Diode), and a camera which makes a mutual fixed angle of, for example, 45°. The focused light source, preferably a laser, emits a beam towards the web, the linear beam being projected as a line on the surface of the material web, this projected line being deflected at a crease or a hole, since the crease bulges upwards or downwards in relation to the rest of the material web, and since the hole represents the absence of material. The deflection of the projected line is registered in the camera and, with the aid of the registered image, it is possible to calculate the position and geometry of the crease in the same manner as the position and the geometry of the hole may be determined. This is termed a measurement in three dimensions (3D).

In addition to the crease lines and possible holes, measurements are taken according to the present invention also of the position of printed, contrasting register markings, which takes place by means of a measurement which may be described as taking place in two dimensions (2D). The register markings indicate the position of the printed pattern. On measurement of a register marking, use is made of a dispersed, diffuse light which has preferably occurred by the reflection of light from a laser line, less preferably from another light source, in order to take an image of the register marking at the same time as the position and geometry of the crease or the hole are determined. When a laser beam or laser line has been reflected towards the surface of a material web, its light is dispersed at different angles out from the surface in a diffuse, unfocused manner. Dispersed light differs from focused light which, for example, comes direct from a laser light source and forms a parallel beam and is not dispersed. When focused light reaches a matt, non-highly reflective surface, such as for example a paper surface, it is reflected in the plane of the paper surface so that it will be illuminated over a larger area. Strictly focused light from a laser light source is also scattered in the paper surface in this manner, for which reason dispersed, diffuse light is also formed from a laser beam which is projected as a line on the surface of the material web. The light dispersion in a material surface is at its greatest if the material consists of paper or paperboard, but also occurs in other surfaces. In particular, such light dispersion takes place in a similar manner also in a plastic-coated paper surface, since the plastic layer then functions as a lens which allows through the impinging light further down to the subjacent paper surface. By utilising the dispersed light from the reflected laser line, no extra light source is needed for the two-dimensional measurement, whereby both measurement apparatus and measurement method are simplified. The term highly reflective surface is here taken to signify shiny metal surfaces and surfaces which function as a mirror.

By means of both of the above-disclosed simultaneous measurements in 3D and 2D, respectively, it is possible in the same image to establish whether the distance from a register marking to at least one crease line and/or a punched hole corresponds to a predetermined value. If the measurement value does not correspond to the predetermined value, a mutual adjustment takes place of the creasing tool, any possible hole-making apparatus and the printing press. Both of the measurements may be carried out simultaneously even at relatively large distances between the printed mark 3 and the crease line 2, for example up to a length of one repeating unit in the printing press, in particular a packaging length, even if the resolution and accuracy in both of the images of register marking and crease line, respectively, will naturally be higher the shorter the distance between them.

According to yet a further aspect of the present invention, the measured position of a register marking is moreover employed for controlling an apparatus for hole cutting, perforation or the like in a subsequent operation downstream in the conversion of the material web. According to this aspect, holes are cut or perforations made by means of a laser, according to known technology, instead of mechanically forming holes in connection with the creasing operation. Employing this cutting apparatus, a pattern of repeated openings is created in the moving material web, these openings for example being intended to form part of an opening device in the final package.

According to the present invention, the measurement of a register marking may thus be employed both for controlling that the creases arrive in the correct position and for controlling a tool which has some effect on the material web. On the basis of the position of the print, it is thus possible to ensure that the creases are in the correct position and that possible openings or perforations come in the right position.

In order to analyse the images in accordance with the foregoing, identify the type of package on the basis of the register marking, and carry out possible corrections of creasing tool, hole-making apparatus and/or printing press, use is made of a computer. In the computer, there are then normally entered predetermined values of the current distances which are to be measured for a specific package type, the package type being identified with the aid of the register marking and the positions of any possible creases.

Further objects and advantages inherent in the present invention will be apparent to the skilled reader of the detailed description below of currently preferred embodiments.

BRIEF DESCRIPTION OF THE ACCOMPANYING DRAWINGS

The present invention will now be described in greater detail hereinbelow, with the aid of currently preferred embodiments and with reference to the accompanying Drawings. In the accompanying Drawings.

DETAILED DESCRIPTION OF PREFERRED EMBODIMENTS

Figure 1:
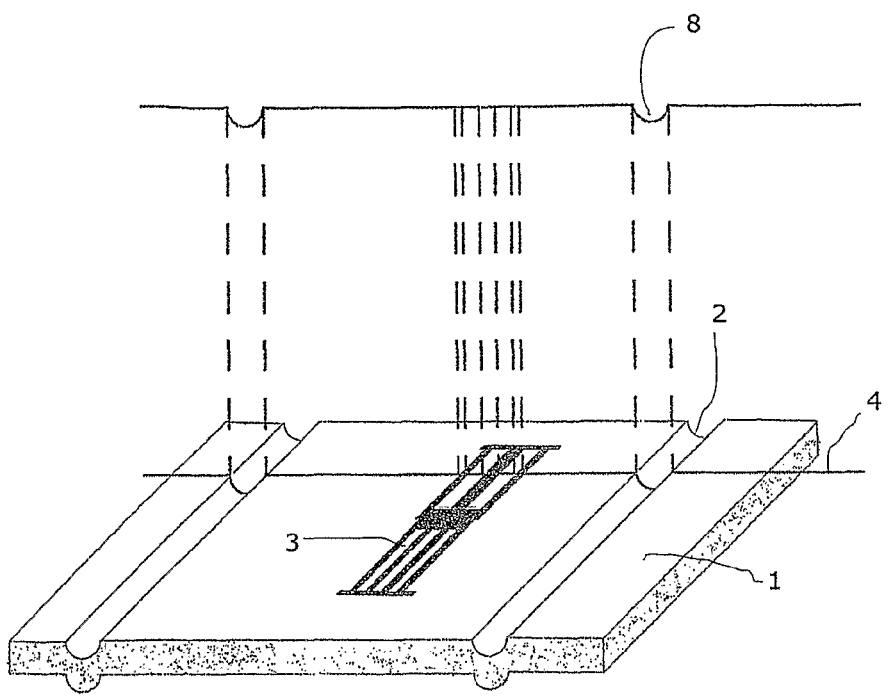
FIG. 1 is a perspective view which schematically illustrates the measurement principle according to the present invention.

Referring to the Drawings, before a material web 1 from which packaging containers for food products or the like are to be formed arrives at a measurement position according to the present invention, it has passed a creasing tool and printing press. In the creasing tool, creases or crease lines 2 are formed along or transversely of the direction of travel of the material web 1. The packages will be folded along these crease lines 2, which form a three-dimensional structure. In the printing press, text and/or images are printed on the material web 1, the print varying depending upon the appearance of the final package. The print includes so-called register markings 3 by means of which it is possible to monitor and control the position of the print. The register marking 3 may be formed in different ways in order, for example, to identify different packages and a predetermined distance to creases 2. The register marking is preferably formed with contrasting panels and constitutes a two-dimensional structure. Normally, the appearance of the different register markings is stored in a computer which is utilized on the identification.

The material web 1 often displays a number of parallel part webs, which may be for the same type of packaging containers or for different types of packaging containers.

Figure 2:
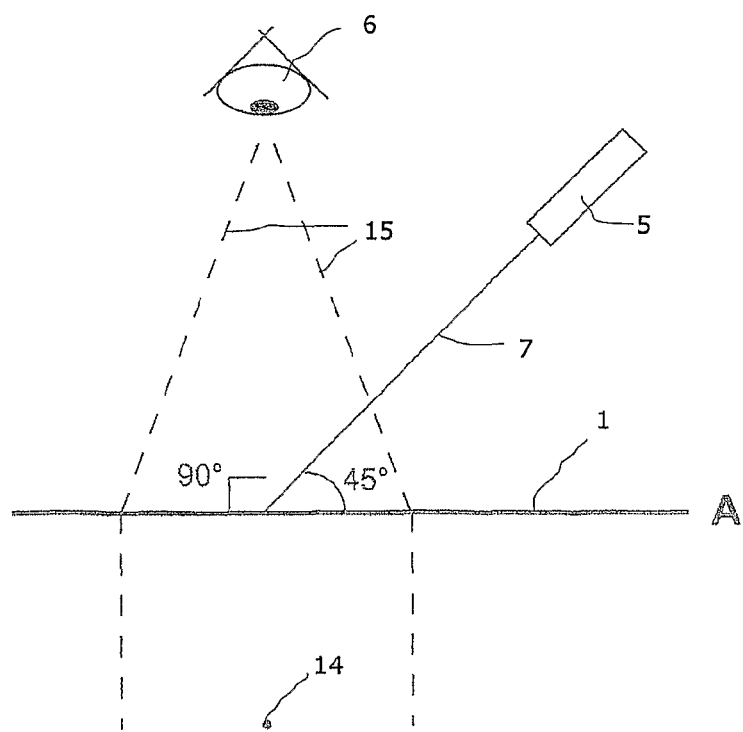
FIG. 2 is a side elevation schematically illustrating the relevant measurement principle.

On measurement and analysis according to the present invention, a laser line 4 is laid in the direction of travel of the material web, as shown in FIGS. 1 and 2, in order to measure transverse crease lines. It is also possible to lay a laser line transversely of the direction of travel, if the intention is to measure longitudinal crease lines. The laser line extends over at least one crease line and one printed register marking.

In the example illustrated in FIG. 2, the illumination with the laser line 4 takes place at an angle of 45° in relation to the material web 1. Straight above the region where the laser line 4 is formed on the material web, a camera 6 is placed in order to reproduce the deflection of the projected laser line caused by the presence of creases or other three-dimensional structures, such as for example holes, in the web. The camera 6 may be, for example, a CCD camera. The laser 5 is thus provided to emit a laser beam 7 at an angle of 45° to the material web 1. The laser line 4 is broken at the creases 2, which is registered by a change of the sensed line 8 in the camera 6, which is intimated in FIG. 1 by broken lines. For sensing and registering of the crease 2, it is of no consequence if the measurement is made from the side with depression, as in FIG. 1, or from the side with an elevation. It is the change of the sensed line 8 which is detected. In FIG. 2, the point 14 signifies the position of the laser beam 7 sensed by the camera 6. By utilizing the dispersed, diffuse light which occurs when the light from the laser line 4 is reflected in the surface of the material web, the register marking 3 is also illuminated and there will moreover be obtained a two-dimensional image of the register marking 3 in the camera 6, which is also intimated by broken lines for the sensed line 8 in FIG. 1.

Using the camera 6, a larger area is sensed, which is shown in FIG. 2 by means of broken lines 15. The register marking 3 and crease lines 2 will thereby be included in the same image, there being obtained the actual distance between register marking 3 and crease line 2 by image analysis. Normally, a number of images is taken during each passage of the relevant register marking 3 and crease line 2, from which images a statistic mean value of the distance is computed. This mean value will then be the value which is given for the distance between register marking 3 and crease line 2 for each package. Those points on the register marking 3 and crease lines 2 from which the distance is measured may vary, but must be well defined in every individual case. For example, it is possible to measure the distance from the centre of the crease 2 to the centre of the register marking 3.

A computer (not shown) is connected to the laser 5 and the camera 6, but also to adjustment apparatuses for the creasing tool and the printing press. In addition, the computer has stored current information for different packaging types, this information being retrieved when, with the aid of register markings, by manual input or by other means the relevant material web 1 has been identified. The computer also carries out the analysis of the images and those computations which are carried out based on this analysis. Since the different parts in the computer are not unique per se, they will not be described further in this disclosure.

The register marking 3, which is normally printed with a dark colour, may also be registered if it lies on a surface printed with another, lighter colour than the register code, as long as there is sufficient contrast between the register marking 3 and the printed surface. In practice, the register marking 3 may be sensed, as long as it is not printed on a dark surface.

Figure 3:
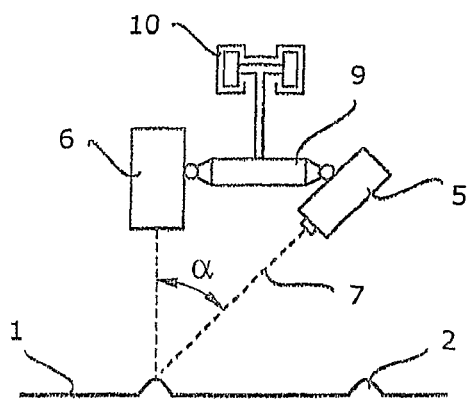
FIG. 3 is a simplified side elevation of one example of a measurement device according to the present invention.
Figure 4:
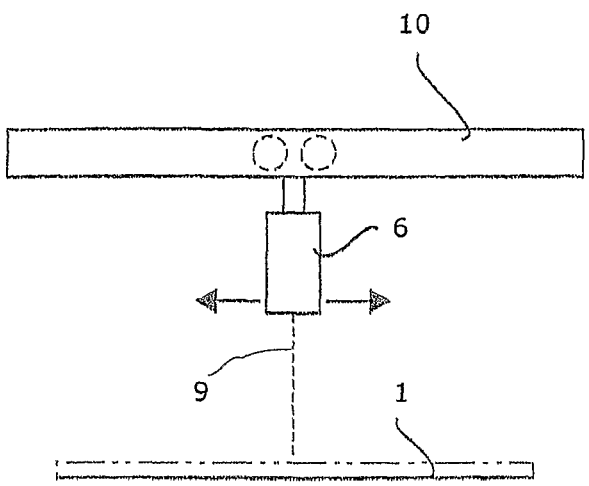
FIG. 4 is an end elevation of the measurement device according to FIG. 3.

In the embodiment illustrated in FIGS. 3 and 4, the laser 5 and the camera 6 are mounted in a common unit. The laser 5 and the camera 6 are mounted on a common bracket 9 which holds the laser 5 and the camera 6 at predetermined mutual positions. The bracket 9 is in turn movably disposed along a rail 10. The bracket 9 is movable by means of wheels which run in the rail 10. The skilled reader of this specification will realise that the unit which comprises the laser 5 and the camera 6 may be disposed in many different ways as regards both construction and mobility. Most generally, double pairs of lasers 5 and cameras 6 are disposed on each bracket 9 where the respective units are mounted at the intended angles in relation to one another.

During a first fine tuning, measurement takes place consecutively web for web on a plurality of parallel webs, in order to register any possible differences between the webs. As disclosed above, there are as a rule a plurality of parallel webs, where the number of webs often varies between three and ten. After the fine tuning, the measurement takes place constantly on a central web, since the relationship of this web to the remaining webs is known and the variations in the remaining webs can thereby simply be computed. The first fine tuning may also be employed for identifying the relevant web and for retrieving from a file in the computer the desired predetermined values which apply to precisely that web. If the statistic mean value deviates from a predetermined, desired distance between register marking 3 and crease line 2, a signal is emitted to the adjustment mechanism for the crease tool and/or printing press to adjust the speed of rotation of each respective unit. Thereby, there will be obtained an automatic adjustment of the distance between register marking 3 and crease line 2 during operation.

By continuous measurement, any possible deviations are detected and may be corrected rapidly. Moreover, this takes place in a closed loop. As a result of the present invention, it is now possible to reduce the tolerance for the distance between register marking 3 and crease line 2 by a factor of ten, compared with prior art technology.

On some packaging types, openings are provided or perforations made in a subsequent operation downstream of the conversion line for the material web. Preferably, this takes place by means of cutting with a laser, according to prior art technology. These openings and perforations may be intended to receive specific opening devices, to receive drinking straws, to facilitate opening of the package, etc. It is crucial that such possible openings and perforations arrive in the correct position in relation to print and crease lines.

In addition to the described use of the present invention, the above described triangulation technology may moreover be employed for determining the thickness of the material web and its position in the lateral direction on adjustment of the conversion process according to the present invention.

Figure 5:
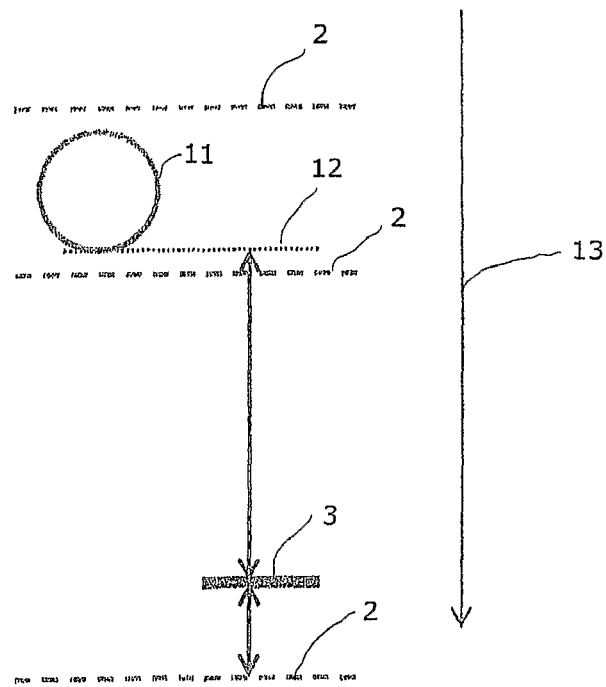
FIG. 5 is a simplified sketch illustrating the control of e.g. a laser cutting device.

According to yet a further aspect of the present invention, the position and registration of the register marking 3 is utilized for controlling a unit positioned downstream in the conversion line, for example a laser cutter, in order to cut a repeated pattern, e.g. a hole 11 or perforations, in the material web 1. The direction of travel of the material web 1 is shown by means of an arrow 13 in FIG. 5. On the positioning of the laser cutter, the point of departure is thus the position of the register marking 3, with corrections for the variation of the distance between print and creases 2. It is hereby possible to place the cut-out pattern, e.g. a hole 11, in the correct position in relation to the print and creases 2 of the package. By forming the register markings 3 in different ways, it is possible to detect whether the relevant package is to be provided with a hole 11 and also control the configuration and size which the possible hole 11 is to have. FIG. 6 schematically illustrates how the position 12 of, for example, a hole or other cutting 11 is determined based on a register marking 3 and its relation to crease lines 2.

What is claimed is:

1. A method for controlling the register between a register marking and at least one three-dimensional structure in a material web for packaging containers, wherein a focused light beam is placed in an intersecting direction to said structure, where the structure is identified by triangulation in a three-dimensional measurement and where the register marking is registered by two-dimensional measurement in dispersed light from a light source.

2. The method as claimed in claim 1, where the register marking is registered by two-dimensional measurement, utilizing dispersed light which occurs by reflection of the light of the focused light beam in the surface of the material web.

3. The method as claimed in claim 1, where the focused light beam is a laser line.

4. The method as claimed in claim 3, where the measurements are carried out with the aid of a laser placed at an angle in relation to a camera placed straight above the measured area and where the distance between register marking and three-dimensional structure is established by image analysis.

5. The method as claimed in claim 4, where the results of the analysis of a plurality of images taken in rapid sequence on the same pair of register marking and three-dimensional structure is utilized for producing a statistical mean value of the actual distance between the register marking and the structure.

6. The method as claimed in claim 1, where the three-dimensional structure comprises a crease.

7. The method as claimed in claim 1, where the three-dimensional structure comprises a hole.

8. The method as claimed in claim 6, where the statistic mean value is compared with a predetermined desired value and the speed of a creasing tool, a hole-making apparatus and/or a printing press is adjusted if the measured value differs from the predetermined value by a certain magnitude and where the size of the change in speed is determined by the difference between measured value and predetermined value.

9. The method as claimed in claim 8, where the hole-making apparatus comprises a punch.

10. The method as claimed in claim 1, where the measurement takes place on one of a plurality of parallel webs, in which event during a fine-tuning phase measurements take place in sequence on all webs in order to identify the different web types and the characteristic distance between register marking and three-dimensional structure for each web.

11. An apparatus for measuring the register between a register marking and at least one three-dimensional structure of a material web for packaging containers as claimed in the method of claim 1, wherein the apparatus comprises a laser and a camera disposed at an angle in relation to one another.

12. The apparatus as claimed in claim 11, where the angle is approx. 45°.

13. The apparatus as claimed in claim 12, where the laser and the camera are disposed on a common bracket, said bracket being movably disposed in a rail.

14. The apparatus as claimed in claim 11, where the laser and the camera are connected to a computer for control, registration and image analysis, said computer also being employed for controlling the speed of creasing tool/punching tool and printing press.

15. The apparatus as claimed in claim 11, where the camera comprises a CCD camera.

16. Use of the method and/or apparatus as claimed in claim 1, wherein the method and/or the apparatus are used to control the position of a unit for repeated cutting-out from a material web.

17. Use as claimed in claim 16, where the position of a register marking is taken as the point of departure from which the position of the desired cut-out is measured.

18. Use as claimed in claim 17, where the measurement of the position for the register marking is corrected with a variation for the distance between print and three-dimensional structure measured previously.

19. Use as claimed in claim 16, where the unit for the cut-out operation comprises a laser cutter.

20. Use as claimed in claim 16, where identification of the register marking is employed for controlling the configuration, size and position of the cut-out.

\* \* \* \* \*